United States Patent [19]
Louis

[11] Patent Number: 5,202,744
[45] Date of Patent: Apr. 13, 1993

[54] ELECTRO-OPTICAL MEASURING INSTRUMENTS

[76] Inventor: Thomas A. Louis, Max-Reger-Strasse 22, D-7032 Sindelfingen 1, Fed. Rep. of Germany

[21] Appl. No.: 669,407

[22] PCT Filed: Jul. 25, 1989

[86] PCT No.: PCT/GB89/00845
§ 371 Date: Mar. 22, 1991
§ 102(e) Date: Mar. 22, 1991

[87] PCT Pub. No.: WO90/01692
PCT Pub. Date: Feb. 22, 1990

[30] Foreign Application Priority Data

Jul. 29, 1988 [GB] United Kingdom ................ 8818106
Sep. 13, 1988 [GB] United Kingdom ................ 8821470

[51] Int. Cl.$^5$ ...................... G01N 21/64; G02B 21/00
[52] U.S. Cl. ....................... 356/73; 356/417; 359/498; 359/502
[58] Field of Search ............. 356/317, 417, 73; 359/487, 498, 502

[56] References Cited

U.S. PATENT DOCUMENTS

| | | | |
|---|---|---|---|
| 4,243,322 | 1/1981 | Ingalz ................................. | 356/244 |
| 4,692,690 | 9/1987 | Hara et al. ........................ | 356/73 |
| 4,744,663 | 5/1988 | Hamashima et al. ............. | 356/73 |

FOREIGN PATENT DOCUMENTS 0164680 12/1985 European Pat. Off. .
84/01029 3/1984 World Int. Prop. O. .

OTHER PUBLICATIONS

Patent Abstracts of Japan, vol. 10, No. 154 (P-463), 4 Jun. 1986 & JP, A, 61008649 (Kogyo Gijutsuin) 16 Jan. 1986.
Patent Abstracts of Japan, vol. 11, No. 292(E-543), 19 Sep. 1987; & JP, A, 62092487 (Fujitsu Ltd.) 27 Apr. 1987.
Patent Abstracts of Japan, vol. 4, No. 110 (P-22) (592), 8 Aug. 1980; & JP, A, 5567718 (Mitsubishi Kasei Kogyo K.K.) 22 May 1980.

Primary Examiner—Richard A. Rosenberger
Attorney, Agent, or Firm—Nixon & Vanderhye

[57] ABSTRACT

The present invention relates to an optical routing module (2) suitable for use in a light microscope (1) for sample inspection simultaneously with a primary light source (10) and a secondary light source (7) of different wavelength. The module (2) comprises a housing mounting first and second polarizing beam splitters PBS1, PBS2 along a primary light beam pathway through the module and having secondary light beam inlet and outlet means (5,6) opposite different ones of the polarizing beam splitters PBS1, PBS2, which have a narrow predetermined operating wavelength range, defined between s- and p-plane transitional wavelengths, which substantially excludes the primary light source wave length band and such that at least one polarizing plane component of each of the secondary light source and a secondary light output from the sample is subjected to a different one of transmission and reflection from that to which the primary light source is subjected at each of the first and second polarizing beam splitters PBS1, PBS2, which are further formed and arranged for defining a secondary light beam pathway from the inlet (5) to the outlet (6) so that the secondary light beam pathway is brought substantially into alignment with an outward leg of said primary beam pathway upstream of the sample by said first polarizing beam splitter PBS1 and is separated back out from a return leg of said primary light beam pathway downstream of the sample by said second polarizing beam splitter PBS2 whereby in use of the module (2) in a light microscope (1), the area of incidence of the secondary light beam with the sample may be monitored via the primary light beam.

25 Claims, 6 Drawing Sheets

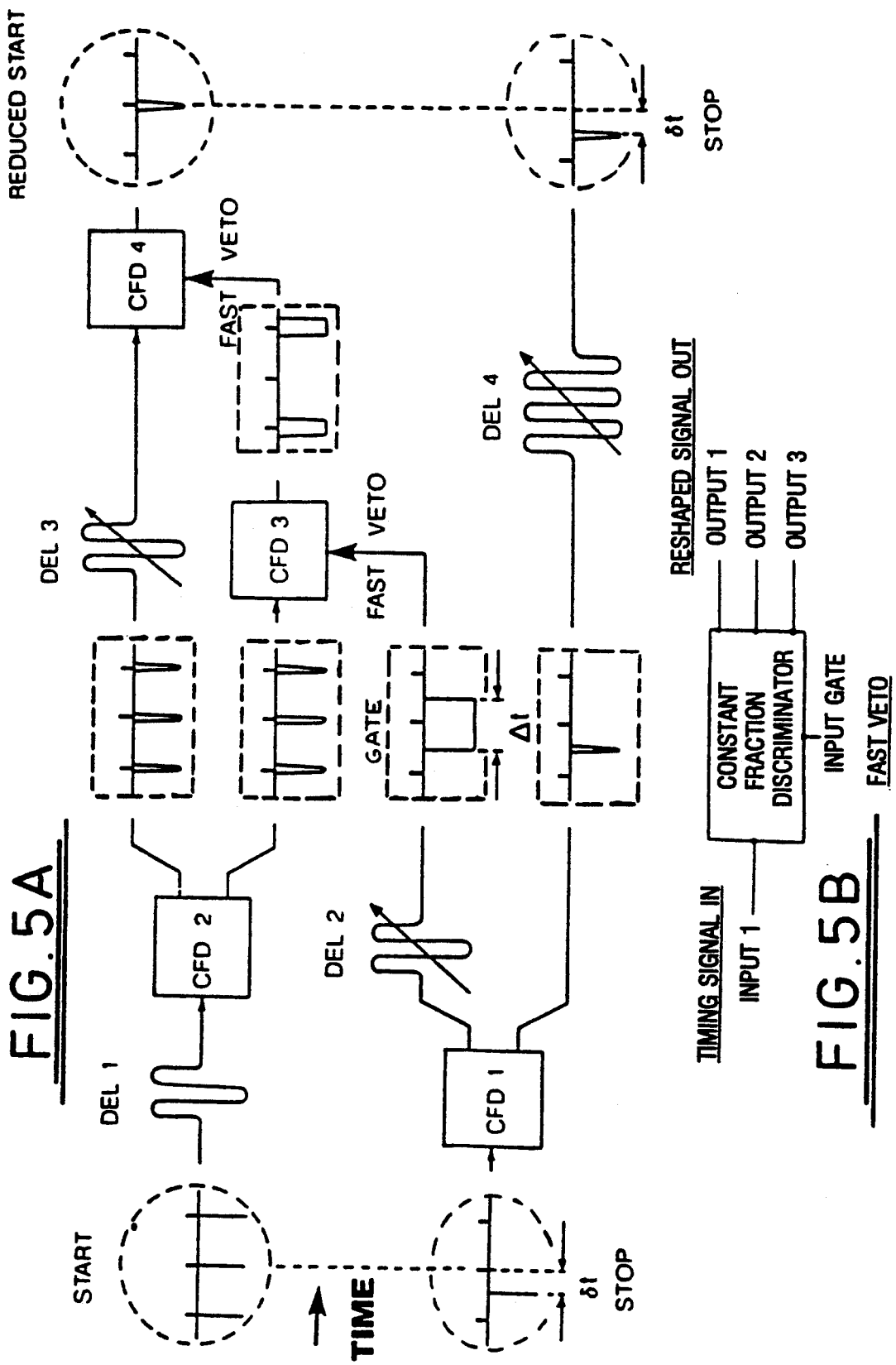

ELECTRO-OPTICAL MEASURING INSTRUMENTS

BACKGROUND OF THE INVENTION

1. Field of the Invention

The present invention relates to electro-optical measuring instruments and to optical routeing modules and gating devices suitable for use therein.

2. Discussion of Prior Art

With ever-increasing miniaturization of electronic circuits there is a need for increasingly sophisticated analytical techniques operating at ever higher resolutions. One such technique involves the use of Photoluminescence Lifetime Spectrometers (PLS) for measurement of photoluminescence in semi-conductors especially those of compounds such as Gallium Arsenide (Ga As) which are more susceptible to the incidence of structural discontinuities due to local crystallisation defects, such defects being detectable by variations in the photoluminescent output thereat.

In more detail, photoluminescence is the emission of a photon upon recombination of an electron-hole pair generated by photoexcitation of a semiconductor. The term photoluminescence is normally used to describe this mechanism in solids, whereas the term fluorescence describes analogous processes in atoms and molecules.

The photoluminescence intensity is related to the number of excited electron-hole pairs, or, in other words, the excess carrier densities. These carriers eventually decay, the carrier lifetime being determined by the rates of decay via various (electron-hole pair) recombination mechanisms. Photoluminescence is the result of a radiative recombination process and can be observed externally, due to photons leaving the sample surface. The carrier lifetime can be determined from the photoluminescence lifetime by straightforward interpretation.

The carrier lifetime and the closely related carrier diffusion length are the most important parameters characterising the electronic properties of a semiconductor In order to predict and explain semiconductor device performance, these two parameters have to be known.

In gallium arsenide (GaAs), the technologically second most important semiconductor after silicon (Si), the carrier lifetime is of the order of 10 ps to 1 $\mu$s ($10^{-11} - 10^{-6}$ s), depending on the influence (presence/absence) of localized non-radiative recombination centers. It is hence obvious that spatial fluctuations of the carrier lifetime can occur on a scale comparable to the carrier diffusion length, typically below 1 to 10 $\mu$m. In fact, strong inhomogeneities in the carrier lifetime have been experimentally observed by averaging over about 100 $\mu$m, i.e. many times the diffusion length in GaAs, but closer investigation has so far been impossible due to lack of an experimental technique.

It is known that integration density of gates on GaAs chips is still very low compared with Si, because of the inhomogeneity of GaAs wafers. hence there is great commercial interest in experimental methods capable of measuring the carrier lifetime of such materials with high temporal and high spatial resolution Time-correlated single photon counting (TCSPC) is an experimental technique for measuring the dynamic behaviour of excited electronic states in atoms, molecules and solids. At present, this technique is widely applied in photochemistry and photobiology with many commercial systems for fluorescence decay measurements already on the market. However, due to lack of fast single photon detectors with high sensitivity in the near infrared, its application to semiconductors has so far been very limited.

It is important to realise, that the TCSPC technique is several orders of magnitude more sensitive than any other experimental technique for measuring time-resolved photoluminescence. This permits the measurement of photoluminescence with very high spatial resolution. With other techniques a large photoexcitation density is required in order to obtain a sufficiently large signal from a small sample area. However, the upper limit for the tolerable excitation density is often the doping concentration. In other cases, e.g. in testing a laser diode resonator structure of typically $50 \times 3 \times 1$ $\mu m^3$ size, the excitation density may have to be even lower in order to stay below the onset of induced emission.

Taking into account only the inevitable losses occurring in the sample itself, internal quantum efficiency, geometric factors, surface reflection etc., the signal intensity available from a sample area of only a few $\mu m$ diameter can be as low as a few photons per excitation pulse. Even with a highly efficient spectrometer, this signal intensity is reduced even further by spectral discrimination etc. before being detected.

Previously known apparatus is unable to separate out and extract such very low intensity output signals at the high spatial resolutions required to pin-point any microscopic defects that may be present on the semi-conductor surface or in the body volume probed by the photoexcited carriers. In addition there is the major problem, once the occurrence of individual luminescence photons has been accurately detected, of measuring the elapsed time between the detected photons and the associated excitation pulses which originally gave rise to them, given the extremely large numbers of excitations pulses for which no output photons are detected, as well as the very high excitation pulse frequencies which are used in practice in these studies.

SUMMARY OF THE INVENTION

It is an object of the present invention to avoid or minimize one or more of the above disadvantages.

The present inventor has now found that by using an optical routeing module of the invention in a light microscope with infinity corrected optics, a secondary light beam pathway can be routed into and out of a primary light beam pathway of the microscope with very high spatial and signal resolution allowing very precise monitoring of the area of incidence of the excitation signal with the sample and extraction of photoluminescent photons output from the primary beam pathway very substantially free of excitation pulse and primary light beam signals.

Thus in one aspect the present invention provides an optical routeing module device suitable for use in a light microscope for sample inspection simultaneously with a primary light source and a secondary light source of different wavelength to said primary light source, which device comprises a housing mounting first and second polarising beam splitter means along a primary light beam pathway through said device and having secondary light beam inlet and outlet means disposed opposite different ones of said first and second polarizing beam splitter means, said first and second polarising beam splitter means each having a narrow predetermined operating wavelength range, defined between s-plane and p-plane transitional wavelengths, which substantially excludes the primary light source wavelength band and is substantially above or below the wavelength band of said primary light source and such that the wavelength band of each of the secondary light source and a secondary light output from the sample responsive to incidence of said secondary light source on a said sample in use of the device is substantially below the s-plane transitional wavelength or above the p-plane transitional wavelength, of a respective one of said first and second polarising beam splitter means, respectively whereby, in use of the device, at least one polarising plane component of each of the secondary light source and said secondary light output is subjected to a different one of transmission and reflection from that to which the primary light source is subjected at each of the first and second polarising beam splitter means, said first and second polarising beam splitter means further being formed and arranged for defining a secondary light beam pathway from said inlet to said outlet so that the secondary light beam pathway is brought substantially into alignment with an outward leg of said primary beam pathway upstream of the sample by said polarising beam splitter means and is separated back out from a return leg of said primary light beam pathway downstream of the sample by said second polarising beam splitter means whereby in use of the device in a light microscope, the area of incidence of the secondary light beam with the sample may be monitored via that small portion of the primary light beam reflected from the sample and leaked through the pair of polarizing beamsplitters into the primary light beam pathway.

With such a routeing module, the primary and secondary light beam pathways are brought together and separated out again at the first and second polarising beam splitters, respectively. In addition, by using a module arrangement wherein a defined polarisation state, i.e s- or p-plane polarization or circular/olliptic polarization, of the secondary light source beam incident upon the sample is altered, e g. by photoluminescence or the elctrooptic effect, the modified secondary beam signal may be very substantially separated from unmodified reflected secondary beam light source signals, even where there is little or no difference in wavelength between the two. Thus the module maximises signal resolution by using polarization discrimination together with spectral discrimination.

It will be appreciated that various different forms of module may be used with diverse spectral characteristics according to the different types of primary and secondary light sources required to be used for any particular sample and/or type of investigation. It may be noted here that modules of the invention may be used for diverse investigations such as fluorecence in microscopic biological samples such as individual plant or animal cells and in electro-optic sampling where voltage charges in microcircuits are monitored through the changes in polarisation they produce in an electrooptically active material such as e.g. GaAs itself.

Thus for example there may be provided different preferred forms of module of the invention depending upon whether the secondary light source has a longer or shorter wavelength than the primary light source, the polarising beam splitters having different transitional wavelengths and, if required, being disposed in different physical arrangements according to which (primary or secondary) beam pathway is to be reflected or transmitted at each of the polarising beam splitters. Naturally additional optical elements may be used as required including for example, polarising plane rotation means such as half-wave plates to change the plane of polarisation of a plane-polarised beam, plane reflecting means such as mirrors and/or plain prisms for changing the direction of a beam, and filters e g. for selective spectral transmission. It will also be appreciated that where there is a significant difference in wavelength between the secondary light source and the secondary light output, the operating wavelength ranges (between the s-plane and p-plane transition curves) of the first and second polarising beam splitters, may be partly offset i e. spectrally shifted relative to each other.

In a further aspect the present invention provides an optical spectrometer device suitable for use in photoluminescence inspection of microscopic areas of microstructures which device comprises a light microscope having infinity corrected optics with a primary light beam pathway from a primary light source to a primary beam image output means, via a sample stage which primary light beam pathway has a substantially common portion extending towards and away from said sample stage, charaterised in that there is provided an optical routeing module device of the invention along said primary light beam pathway common portion, together with a secondary light beam source and a secondary light beam detector means coupled to respective ones of said secondary light beam inlet and outlet means of said module, whereby the position of incidence of said secondary light beam on said sample may be precisely directed by montoring of said primary beam image output means.

Conveniently, for photoluminescence studies especially the secondary light beam source comprises a laser source. With the high resolutions and sensitivity provided by the present invention it is moreover feasible to employ a pulsed diode laser source despite the relatively low power of such means. This in turn is particularly advantageous since it avoids the need for the relatively cumbersome and delicate bench mounted modelocked and/or cavity dumped solid state or gas, lasers, thereby making the spectrometer significantly simpler, more portable and economical than was previously possible. Moreover the use of optical fibre coupling means makes the apparatus significantly more flexible and easier to align.

Any suitable optical processing means may be coupled to the secondary light beam outlet of the module including one or more of a solid state detector, a fibre optic monochromator, and wavelength-division- multiplexer. Most desirably there is used a single photon avalanche diode detector, attached to the outlet directly, fiberoptically, or via spectral discriminating means.

In order to maximize the temporal resolution of the spectrometer, the present invention provides in yet another aspect an anti-coincidence gating means comprising first and second discriminator pulse processing means for receiving respective ones of an excitation signal input comprising a series of pulses corresponding to the laser source secondary light beam pulses and a detector signal output comprising a series of pulses corresponding to secondary light output pulses induced by incidence of said laser source pulses with the sample in use of the device, said first pulse processing means being formed and arranged for providing first and second outputs comprising a first series of pulses corresponding to the laser source pulses substantially free of interference, said second pulse processing means being formed and arranged for providing a first output comprising a second series of pulses corresponding to secondary light output pulses substantially free of interference and a second output comprising a second series of gate pulses for respective ones of said secondary light output pulses temporally extended to not longer than the period between successive said laser pulses; a third pulse processing means formed and arranged for receiving the second output of said first pulse processing means and said gate pulses and providing a modified output corresponding to said first series of pulses from which have been removed, by said gate pulses, those pulses associated with said secondary light output pulses thereby providing an anti-coincidence series of pulses; and a fourth pulse processing means formed and arranged for receiving said first output comprising a said first series of pulses and said modified output comprising said anti-coincidence series of pulses, and combining them so as to provide a reduced output comprising pulses corresponding to only those of said laser pulses for which a secondary light output pulse has been received, said gating means further including pulse delay means formed and arranged for providing said first output of secondary light output pulses in the same temporal relationship to said reduced output of pulses corresponding to corresponding laser pulses, as in the excitation signal input and detector signal output whereby monitoring of said temporal relation is substantially free of interfernce from excitation signals for which no detector signal output is received.

The anti-coincidence gating means of the invention is of a particularly convenient and economic form.

BRIEF DESCRIPTION OF THE DRAWINGS

Further preferred features and advantages of the invention will appear from the following detailed description given by way of example of some preferred embodiments illustrated with reference to the accompanying drawings in which:

FIGS. 5A and 5B are block diagrams illustrating the anti-coincidence gating means of the invention and its mode of operation;

DETAILED DESCRIPTION OF PREFERRED EMBODIMENTS

Figure 1:
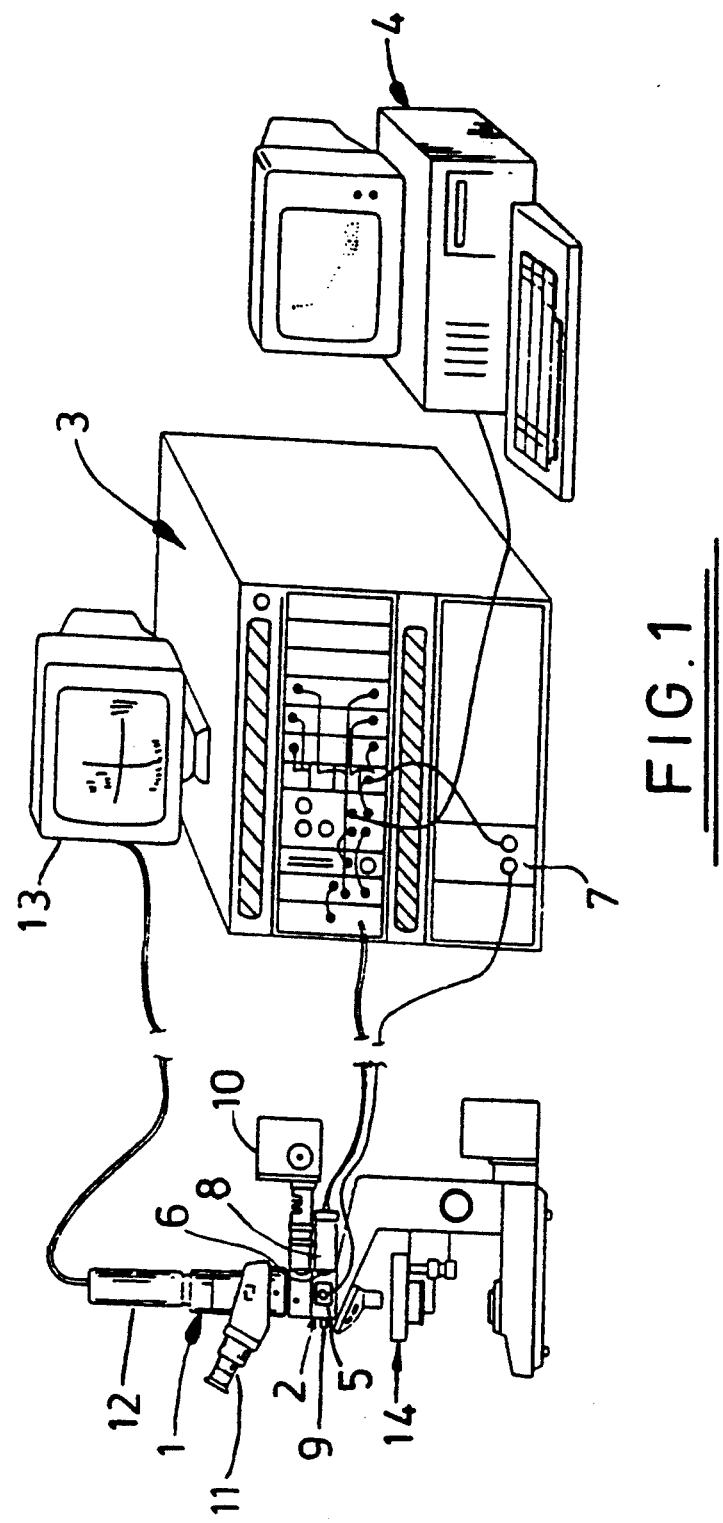
FIG. 1 is a general view of a photoluminescence lifetime spectrometer of the invention with its associated signal processing equipment.

FIG. 1 shows a photoluminescence lifetime spectrometer (PLS) comprising a light microscope 1 which has infinity corrected optics and an optical routeing module 2 of the invention, signal processing apparatus 3, for processing the secondary beam output of module 2 and its temporal relation the secondary beam input to module 3, and data analysis means for converting the output signals from the signal processing apparatus 3 into a useful form.

In more detail the microscope 1 has infinity corrected optics, i e a point source in the object plane forms a parallel beam within the microscope optical column. This allows variation in the optical path length, e.g. by extending the length of the microscope tube and inserting a number of plan-parallel optical components into the beam path, without affecting the image quality. Several commercial microscope systems now have this feature. In the present embodiment an Olympus metallurgical series BH2 microscope was chosen for its convenient modular design, which makes it very easy to split the optical column in the parallel beam region of the microscope and insert the optical routeing module 2 (ORM). The ORM 2 has inlet and outlet ports 5, 6 for coupling a secondary light pulsed laser excitation source 7 into the microscope 1 and suitable detector 8 for secondary light photoluminescence signal photons out of the microscope 1. Optional ports 7 are provided to pick up a synchronisation signal off the pulsed laser light and pick up scattered excitation light for measuring the instrumental response profile.

In other respects the microscope 1 is of generally conventional form having a primary light source e.g. visible or N1R light illuminator 10 an optional binocular eyepiece 11, and a CCD camera 12 coupled to a monitor 13. It will be appreciated that the ORM 2 requires to provide for proper routeing of each of the following:

1 a primary light beam comprising visible light from the microscope's illuminator 10 to a sample disposed on the sample stage 14 of the microscope 1 and thence back to the CCD camera 12 and binocular eyepiece 11 for inspection of the sample through the optical microscope 1;

2 a secondary beam input comprising visible/near-infrared pulsed laser light from the laser excitation source 7 to the sample for excitation of photoluminescence and from the sample surface scattered and reflected back off into the CCD camera 12 and binocular 11 for alignment, laser beam focusing and positioning on the sample; and 3 near-infrared photoluminescence photons from the sample to the detector 8 for time-correlated single photon counting.

If maximum spatial resolution and/or maximum signal collection efficiency of the spectrometer is desired, one has to use optics with high numerical aperture (N.A.) for focusing the excitation light on to the sample and collimating the hemispherically emitted photoluminescence photons. The working distance then reduces to only a few millimeters, which automatically excludes conventional geometries with different axes for excitation and detection such as the well-known L- and T-geometry used in fluorometry.

As a result, excitation light and photoluminescence have to be handled through the same microscope objective and signal separation becomes a problem.

The targets to be met by the ORM design are as follows:

i) suppression of excitation light in the detection channel ii) high photoluminescence signal collection efficiency iii) diffraction limited performance iv) no degradation of optical microscope performance v) modular design vi) definition of simple interfaces for all optical ports vii) low cost All optical signals into or out of the spectrometer can be handled through single-(and multi-mode) optical fibres. This is possible because of the low optical power levels required in the PLS and the ability of this kind of system, due to its highly linear instrumental response, to correct for the linear dispersion of short optical pulses in the fiber of convolution analysis. Detaching the detector 8 from the ORM is optional when using filters instead of a monochromator for spectral selection. It is, however, a very attractive option, as it enhances modularity and has some very specific advantages when used in connection with Single Photon Avalanche Diode (SPAD) detectors in preferred forms of the invention. The use of high precision fibre-optic connectors for linking up the ORM 2 with the sources and detectors mounted in an instrumentation rack and housing the signal processing apparatus 3 or, alternatively, any other external laser source, monochromator or detector, defines a simple, stand optical interface and substantially eliminates alignment problems. All high-speed Nuclear Instrumentation Method (NIM) electronics as well as active secondary beam optical units can be conveniently fitted into such an instrumentation rack. This eliminates the need for transmitting any high speed electronic signals along lossy, inherently noisy coaxial lines outside the instrumentation rack. The detachable instrumentation rack and the data processing apparatus can then be placed at a convenient distance from the microscope 1, e.g. when the latter is to be used in a cleanroom environment.

Figure 2:
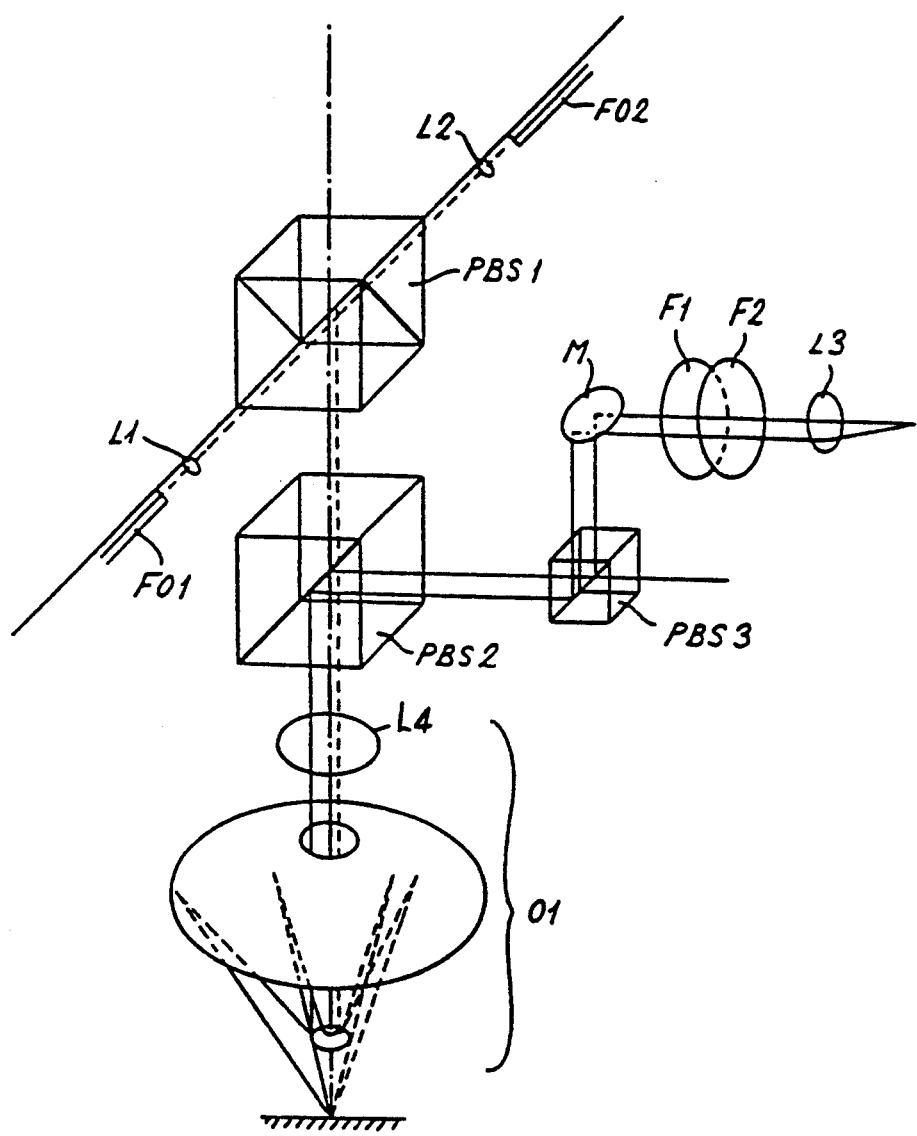
FIG. 2 is a schematic perspective view showing the principal optical components of the optical routeing module and associated microscope objective of the spectrometer of FIG. 1.

FIG. 2 shows the principal parts of a First optical routeing module of the invention together with the reflecting objective 01 of a microscope in which it is being used.

Linearly polarised pulsed laser light is coupled into the ORM by means of polarisation preserving single-mode optical fibre FO1. The polarisation axis is perpendicular to the plane defined by the microscope axis and the direction of propagation of the incoming laser light. The optical fibre/cable is terminated with a polarisation preserving single-mode fibre-optic connector which plugs into a mating adapter of the ORM housing.

A precision lens L1 with very short focal length is fitted into the ORM side of the mating adapter. The divergent beam from the fibre end is collimated by this lens for form a parallel beam with approximately 0.9 mm beam waist diameter.

Precise alignment and a suitable beam steering mechanism is crucial for achieving high spatial resolution with the PLS spectrometer. It is here where the use of optical fibres is most appreciated. As mentioned before, the laser beam exiting the optical fibre is collimated by the precision lens L1 fitted into the mating adapter. The axial distance between the fibre end and the lens is initially adjusted by monitoring the laser spot size produced on the sample, through the microscope.

Manipulation of the excitation laser beam along 4- axes with respect to the ORM is achieved by mounting the mating adapter on a small roll-tilt and x-y translational stage. by simple adjustment of the position and orientation of the mating adapter, the collimated laser beam is initially aligned to be parallel to, but with its axis displaced several millimeters from the microscope's optical axis, as for the reasons mentioned below. The optical source can then be disconnected and reconnected to the spectrometer without loss of alignment. this is considered very important in practice, as it eliminates tedious alignment after transport, allows simple insertion/removal of different ORMs and greatly enhances overall system flexibility.

Figure 3:
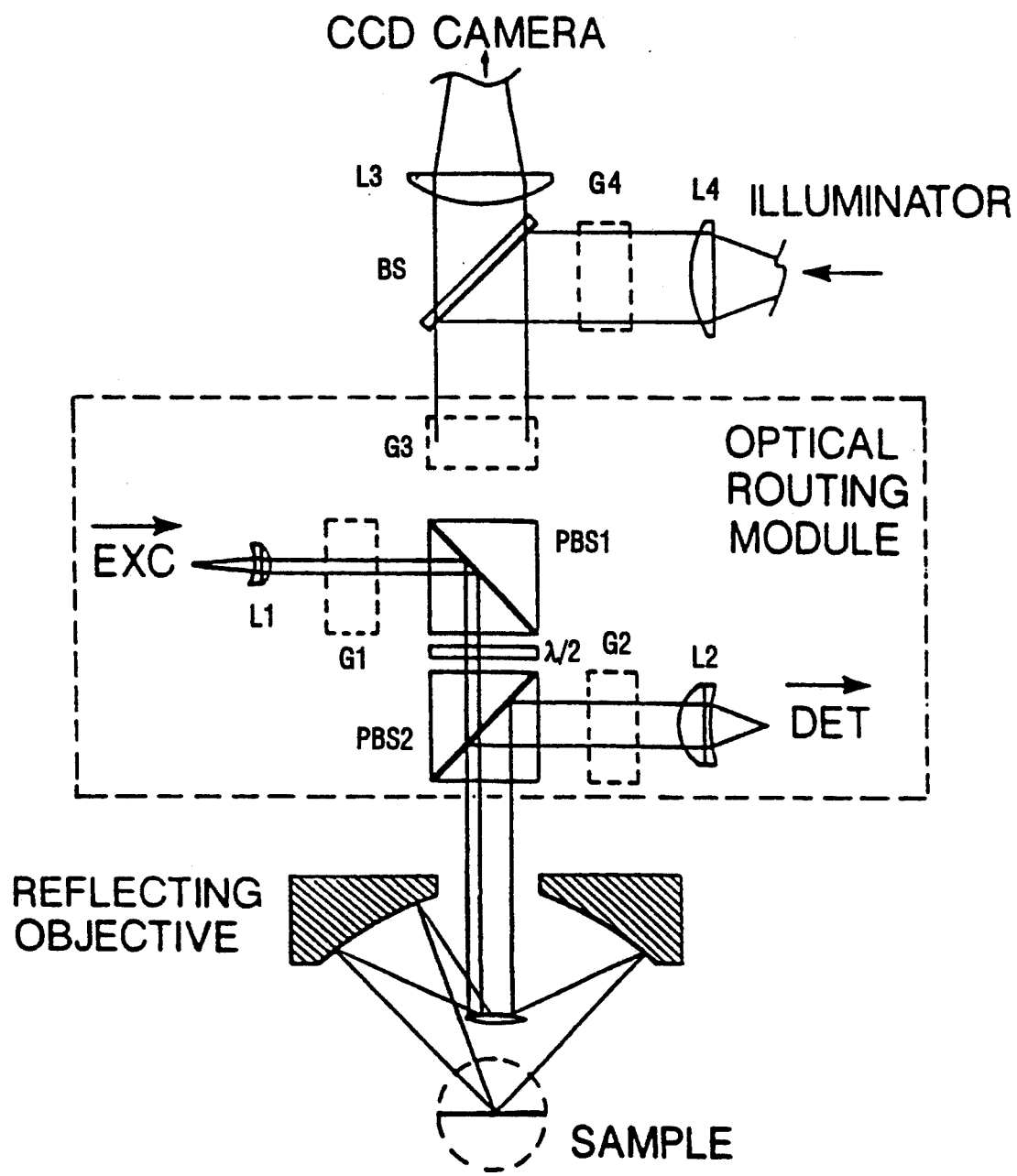
FIG. 3 is a sectional view of a generally similar module showing its relation to the other parts of the microscope of the spectrometer.

As may also been seen in FIG. 3, which is a schematic sectional view of a generally similar ORM shown incorporated in a light microscope of the general type shown in FIG. 1 (this embodiment also including a half-wave plate $\lambda/2$ for changing the plane of polarisation of the excitation beam and various optically plane elements G1–G4 such as filters), the collimated beam is bent 90° down the microscope column into alignment with the primary light beam by a first polarising beamsplitter cube PBS1. Following PBS1, which couples the laser light from the excitation channel into the microscope, a second polarising beamsplitter cube PBS2, couples the photoluminescence signal from the sample out of the microscope and into the detection channel.

Polarising beamsplitter cubes were chosen rather than any other type of beamsplitter because these are optimised for operation within a small wavelength range, typically between 0.9 and 1.1 times the design wavelength. Within this range, the propagation axis of light polarised in the s-plane (with respect to the PBS) is bent by 90°, while light polarised in the p-plane is transmitted. Light of shorter wavelength than 0.9 times the design wavelength is transmitted irrespective of its polarisation state, light of longer wavelength than 1.1 times the design wavelength is reflected irrespective of its polarisation state. By virtue of this property, a pair of crossed polarising beamsplitter cubes do not prevent light from passing through their common optical axis, except within the small wavelength range of operation around the design wavelength.

Figure 4A:
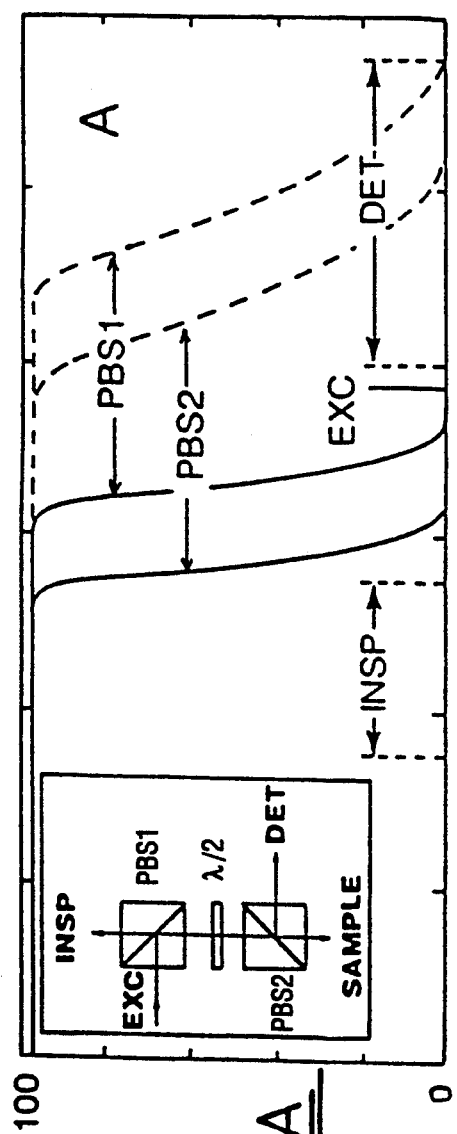
FIGS. 4A and 4B are schematic sectional elevations of two optical routeing modules for use in application with different spectral requirements, shown together with the spectral transmission characteristics of the polarising beam splitter of the respective modules.
Figure 4B:
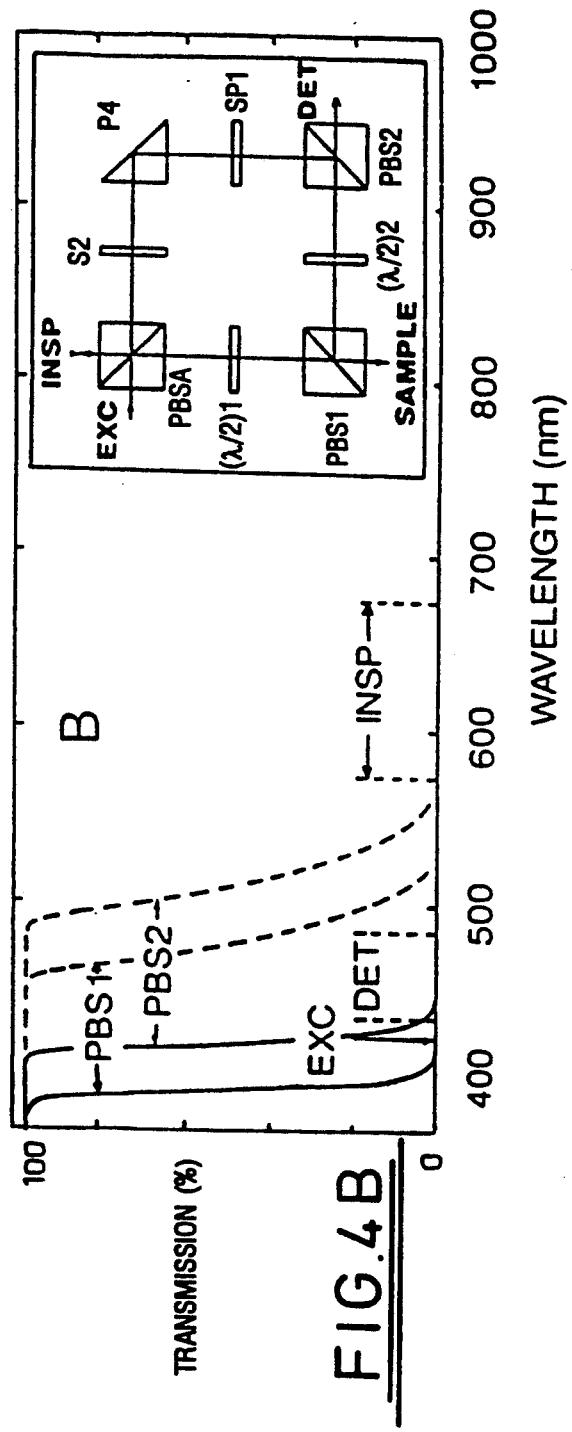

If two distinct wavelength ranges are used for optical inspection of a sample and excitation/detection of photoluminescence, the addition of the ORM to an optical microscope will not affect the microscope's performance. Thus for example as illustrated in FIG. 4A photoluminescence can be excited e.g. at 780 nm EXC and detected at 790–950 nm DET, which is ideal e.g. for investigating the important substrate materials gallium arsenide (GaAs) and indium phosphide (InP). Visible light in the range 400–700 nm passes through the crossed polarizing beamsplitter cubes unhindered, except for rather strong reflection of that part of the visible spectrum which is far off the design wavelength of the anti-reflection coating applied to selected surfaces of the polarizing beamsplitter cubes. In order to obtain best contrast along the INSP pathway whilst retaining a large field of view for inspection (i.e. reflections have to be reduced other than by spatial filtering along the INSP beam pathway), the wavelength range of the visible spectrum used for inspection may be deliberately limited to 575–675 nm as shown in FIGS. 4A, 4B, i.e. close to the operating wavelength of the polarizing beamsplitter cubes. In more detail, it may be seen that the first polarising beamsplitter PBS1 has an operating waveband in the region from 720 nm (boundary between transmission (shorter wavelength side to left of curve) and reflection (longer wavelength side to right of curve) for s-plane polarised light (solid curve)) to 880 nm boundary between transmission and reflection for p-plane polarised light (dashed curve). The operating band of PBS2 may be seen to be offset relative to that of PBS1 to the range 690 to 850 nm. Thus for each PBS, substantially all light of shorter wavelength than the operating band is transmitted and that of longer wavelength is substantially all reflected whereas within the range only p-plane polarised light is tramsitted and only s-plane polarised light is reflected.

Thus in the arrangement shown in FIG. 4A on s-plane polarised excitation source secondary beam is reflected at PBS1 into the primary beam pathway down through the half-wave plate $\lambda/2$ where it is rotated by 90° into p-plane w.r.t. PBS2. The p-plane polarised excitation source secondary beam is then transmitted down through PBS2 onto the sample. Excitation light EXC (s- or p-plane w.r.t. sample surface) specularly reflected off the sample surface is again transmitted back through PBS2, as also is the p-plane polarised component of the randomly polarised photoluminescence emitted from the sample in response to incidence of excitation light thereon. The s-plane polarised component of the photoluminescence is however reflected at PBS2 and thereby separated out from the return leg of the primary light beam pathway thereat and then passes on to the detector.

In the embodiment of FIG. 2 it will be noted that the excitation and detection wavelengths EXC, DET are substantially shorter than the primary light beam wavelengths INSP and the operating wavebands of PBS1 and PBS2 correspondingly shifted to the shorter wavelength and of the spectrum so that in this case all the primary light beam is reflected at PBS1 and PBS2 rather than transmitted there through. This calls for a slightly different arrangement of PBS1 and PBS2 with the ORM including an additional polarising beamsplitter PBSA acting simply as two plane reflectors for each of the primary light beam INSP and the secondary light excitation source EXC. The latter is directed down through a halfwave plate $(\lambda/2)1$ as before to change the polarisation plane of EXC from s- to p- before passing PBS2 and impinging upon the sample. As before the specularly reflected excitation light passes back through PBS1 as does also the p-plane polarised component of the photoluminescence. The s-plane polarised component of the photoluminescence DET and the primary light beam INSP are both reflected at PBS1 and then passes through a second haf-wave plate $(\lambda/2)2$ where the s-plane component of DET is rotated 90° and changed to p- relative to PBS2. Both primary and secondary light beams then continue on to PBS2 where the primary light beam INSP is again reflected to pass back through a first plane spacer SP1, off a plane reflector prism P4 through a second plane spacer S2, to be once more reflected at the additional polarising beam splitter PBSA. the p-plane polarised secondary light beam DET is however transmitted through pBS2, and is thereby separated out from the primary light beam pathway thereat.

Naturally other arrangements based on similar optical principles are also possible for other circumstances e.g. where the excitation wavelength EXC is shorter than for the primary light beam waveband INSP whilst the secondary light output wavelength band DET is longer than the primary light beam waveband INSP. Polarising beam splitter cubes are commercially available across substantially the whole of the visible and near infrared spectrum so that ORMs according to the invention may be readily provided for a wide range of specific applications.

As noted above a reflecting objective (two mirror surfaces) 01 is preferably used instead of a conventional refractive microscope objective (many lenses), because it has a large working distance with no unwanted reflections or chromatic aberration.

In contrast, conventional refractive microscope objectives, optimised and anti-reflection (AR) coated for the wavelength range of visible light, would produce unwanted backscattering signals when used in the near infrared and suffer from chromatic aberration. In picosecond pulse experiments, a narrowband AR-coating optimised for the detection wavelength would be required to suppress multiple reflections, which would broaden the pulse width or produce spurious peaks in the decay curve.

In addition, narrowband coatings perform very badly outside the very small wavelength range around their design wavelength, such as at the excitation wavelength or at the shorter wavelengths used for optical inspection in the PLS.

Reflective objectives do not have these drawbacks. A characteristic feature of these reflecting objectives is the central obstruction, which means that light travelling down the microscope column on or near to the optical axis is reflected back into the microscope instead of being passed through the objective. Because of this, the excitation laser beam is not expanded to the full objective aperture, but only to a rather small beam width, such that it is sent through the reflecting objective between the central obstruction and the limit of the aperture without suffering back-reflection.

The converging laser beam thus forms a narrow light cone incident upon the sample surface at an angle. Reflection of excitation Light off the sample surface is undesirable and can be minimised by passing the laser beam through the reflecting objective such that the beam is polarised in the p-plane with respect to the sample surface. For very high N.A. objectives and/or low refractive index samples, the angle of incidence of the excitation laser beam may approach the Brewster angle, at which no light is reflected off the sample surface at all.

Photoluminescence is emitted from the sample istropically, i.e. hemispherically and randomly i.e. unpolarised. In order to achieve high collection efficiency, a reflecting objective with high N.A. (e.g. N.A.=0.65) is desirably used. The polarising beamsplitter cube PBS2 couples out only the photoluminescence component polarised perpendicularly to the excitation laser beam, i.e theoretically 50% of the total unpolarised signal.

In practice, polarising beamsplitter cubes suppress the unwanted polarisation component with respect to the signal by only about 99%, therefore the photoluminescence signal is desirably further purified by passing it through a further polarisation selective component (see FIG. 2). Use of a polarising prism or a further polarising beamsplitter cube (PBS3) results in discrimination of the photoluminescence signal with respect to back-scattered excitation light by a factor of at least $10^4$.

The photoluminescence signal then desirably is further discriminated spectrally, which can be achieved either with narrowband interference and/or long-pass filters or with a suitable monochromator.

However, although spectral selection discriminates against scattered excitation light and possibly ambient light leaking in, it cannot discriminate against multipy reflected photoluminescence photons at the detection wavelength. As the reflectivity of even AR-coated optical surfaces is of the order of 0.5-1%, this will normally show up as replicas of the decay, shifted with respect to the peak of the principal decay by a time equivalent to the distance between the optical surfaces involved (1 mm =8 ps at the speed of light) and with correspondingly smaller amplitudes.

This drastic effect was first observed when using a very small area detector in a time Correlated Single Photon Counting (TCSPC) set-up. It was found, after discriminating the photoluminescence signal against scattered excitation and ambient light by polarisation selective and spectrally selective elements, that a further step, spatial filtering, was desirable to discriminate the main photoluminescence signal against delayed, multiply-reflected photons in order to minimise pulse broadening (at low time resolution, slow decays) or the appearance of replicas (at high time resolution, fast decays) in the decay curve.

Spatial discrimination may be achieved in the PLS/ORM by refocussing the collimated photoluminescence signal and defining a small aperture in the image plane. The small size of the aperture, typically 5-20, microns diameter, makes it the system stop aperture. The spatial resolution of the spectrometer is then given by the field of view of the detector as defined by the diameter of the stop aperture in the image plane and the magnification of the optics. Definition of the spatial resolution of the system through the spectrometer field of view rather than through the excitation spot diameter has two important advantages. Firstly, the photoluminescence signal is discriminated against multiple reflections or "ghost images". Signal photons crossing refractive optical surfaces at an angle with the surface normal will be scattered slightly out of the main beam path. In the prototype PLS it was found that spurious reflections, especially from the surfaces of the polarising beam splitter cubes, disappeared completely, once the stop aperture was correctly positioned in the image plane. This may conveniently be achieved by slightly tilting the planar optical components in the parallel beam path by a few degrees with respect to said optical axis, (i.e. the direction of signal propagation). Normally, the inevitable misalignment of the beamsplitter cubes due to ordinary fabrication tolerances for the ORM mechanical housing will be sufficient to produce this desirable effect. Secondly, if the field of view of the spectrometer is much smaller than the excitation spot size, the excitation density across the field of view will be almost homogeneous. This simplifies the physical interpretation of the resulting photoluminescence decay in terms of a one-dimensional excitation density profile, i.e. a variation with depth only. Otherwise, for very small excitation spot sizes (several $\mu m$ diameter) lateral diffusion of carriers out of the detector field of view would have to be taken into account.

Ideally, if diffraction were negligible, the field of view of the spectrometer would be a well-defined circular area e.g. at the centre of the excitation spot, its radius being smaller than the excitation spot radius by at least several times the carrier diffusion length. In practice, diffraction will slightly smear out the abrupt spectrometer field of view, which in the geometrical case and with no vignetting present, is a simple step function defined by the diameter of the stop aperture. The maximum excitation spot size will also normally be limited by the power available from the excitation source, especially when using a pulsed laser diode.

The separated out photoluminescence signal available at PBS3 can be used to measure the instrumental response through a separate channel, simultaneously with the photoluminescence decay. This instrumental response channel will be identical to the photoluminescence detection channel, except that the spectrally selective element, filter or monochromator, is set to the excitation wavelength. Simultaneous acquisition of photoluminescence and (scattered) excitation signal in the PLS would require duplication of the detector, time-convertor (TAC) and analog-to-digital converter (ADC) because of the very high data collection rate of approximately 100 kHz (=0.2% of 50 MHz) to be handled under optimum conditions by each channel.

The PLS can be used with pulsed laser diode excitation and single photon avalanche diode (SPAD) detection. This is a major advantage over any other comparable system, whether it is a conventional TCSPC system with a micro-channel plate photomultiplier (MCP-PMT), a streak camera system (=time-domain methods) or a system with a phase sensitive detector (frequency domain method). These other systems always require a large, powerful and expensive laser source, usually a synchronously pumped picosecond dye laser system.

The use of only solid state components, i.e. a laser diode source and a SPAD detector, and the possibility of mechanically decoupling source and detector from the microscope sample stage via optical fibre connectors, allow a simple, rugged and economically priced system to be provided in accordance with the present invention. The low power density requirements of the PLS allow use of optical fibres for interconnections, thus enhancing the modularity and flexibility of the optical system, easing alingment and eliminating the need for an optical bench/table.

The photoluminescence output detected by the SPAD then requires to be processed to allow measurement of the photoluminescent lifetime delay characteristics of the sample volume under inspection. The rapid decay of photoluminescence in GaAs substrates allows to take full advantage of the high repetition rate (up to 100 MHz) of commercially available pulsed laser sources. Theoretically, this permits a data collection rate of 500 kcps (0.5% of 100 MHz) without risking distortion of the data due to statistical pulse pile-up. In practice, the maximum data collection rate is limited to around 100 kHz due to the finite conversion dead time of even the fastest commercially available time-to amplitude converter (TAC), the Tennelec TC 863 (min. 1.6 $\mu s$ dead time) and analog-to-digital converter/multichannel analyser combination (ADC/MCA9, the Silena Mod. 7423/UHS ADC and Mod. 7328 MCA/buffer (3 $\mu s$ fixed dead time). However, strong non-linearities in the response of all commercial TACs are observed when the TAC is subject to low count rate random START signals and the STOP input is triggered with a periodic signal at a frequency above 10 MHz. Obviously, NIM electronic devices such as the TAC are designed to operate with random signals up to $3 \times 10^7$ cps in the STOP and START branch, but not with periodic signals as in TCSPC. For this reason, cavity dumping has so far been considered essential in TCSPC. This has certainly not stimulated widespread application of the TCSPC technique, as the need for cavity dumping, usually available only in connection with a synchronously pumped dye laser system, is clearly a disadvantage with respect to other TRPL methods capable of operating at the high (76–100 MHz) mode-locking frequencies of a simple Nd:YAG or ion laser.

So far, reduction of the high repetition rate signal to the much lower PL signal rate by form of coincidence gating, has, although proposed in the literature, not been widely used in TCSPC experiments. FIGS. 5A and 5B show a new two stage anti-coincidence gating circuit. In more detail the circuit makes use of four cascaded constant fraction discriminators (CFD1–CFD4), such as the commercially available Phillipps Scientific Mod 714 QUAD CGD, and eliminates the need for any purpose built hardware. The circuit shown also includes delay means in the form of three variable coaxial delay lines DEL2–DEL4) and one fixed delay coaxial cable (DEL1).

Three successive START pulses out of a continuous train of pulses corresponding to the secondary beam laser excitation pulses are shown in FIG. 5A. In this particular example, the second START pulse is associated with a single STOP pulse corresponding to a photoluminescence pulse induced by the laser excitation pulse to which the second START pulse corresponds, which is delayed with respect to the START pulse by $\delta t$. (In TCSPC, the statistical distribution of $\delta t$ over a large number of events produces a histogram approximation of the photoluminescence decay characteristic). The START pulse is deliberately delayed relative to the STOP pulse by DEL1. This allows a GATE pulse triggered by the STOP pulse in CFD1 to overlap the leading edge of the shaped second START pulse output from CFD2 present at the input of CFD3. The width of the GATE pulse is precisely adjusted to be $\Delta t$, the START pulse spacing. Synchronization of the reshaped second START output from CFD2 and the GATE pulse from CFD1 is achieved by varying the delay DEL2. The second START pulse corresponding to the STOP pulse is eliminated in the output from the anti-coincidence gated CFD3. The CFD3 output is used to anti-coincidence gate CFD4 so as then to produce a desired REDUCED START pulse train from the shaped, delayed and synchronized second output of CFDI, which comprises only those START pulses for which a corresponding STOP pulse has been received.

Any TCSPC system operating at high repetition rates (1 MHz) will benefit from the described circuit in three ways.

1 The periodic oscillations in the TAC response, due to the high repetition rate periodic input, disappear.

2 The TAC can be operated in normal, i.e. non-inverted mode.

3 The useable time window $\Delta t$ can be placed anywhere within the full TAC range.

As a result, the non-linearity of typically more than 2% at repetition rates (STOP) above 10 MHz are reduced to the values specified for standard operation, typically less than 0.8% (specified <1%).

In addition, in MCAs using Wilkinson type ADCs for converting the TAC output, the overall conversion rate is strongly improved when the decay peak is placed into a low channel. At very high repetition rates, e.g. 100 MHZ, the width of the useable time window, $\Delta t$, is increased significantly, e.g. by shifting the window away from the beginning of the TAC range, which is adversely affected by a fixed amount of dead time and high non-linearity. At 100 MHz repetition rate, the useable time window $\Delta t$ is hence increased from less than 4 ns to almost full pulse spacing −10 ns, an increase of more than 100%.

FIG. 5B shows generally the connections to a constant function discriminator when used in a fast veto gating mode as in the case of CFD3 and CFD4.

Figure 6A:
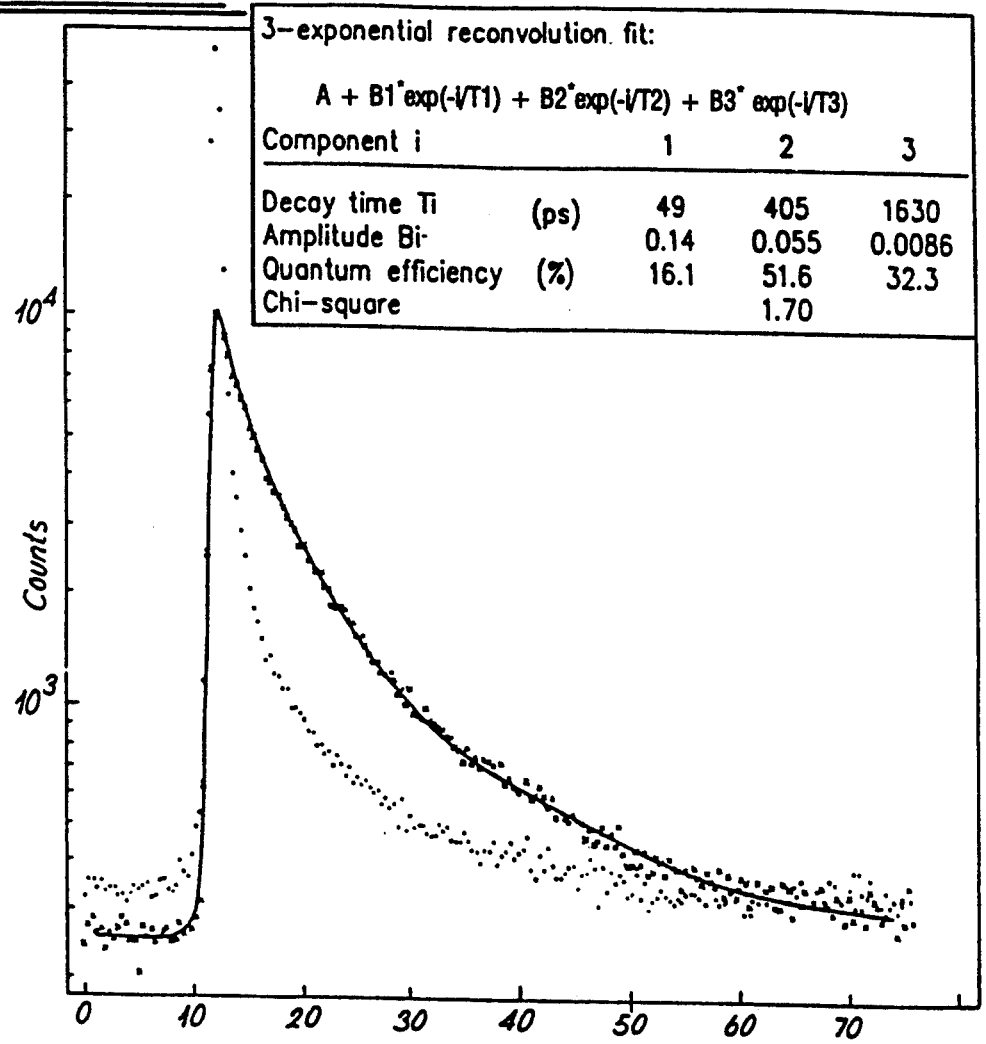
FIGS. 6A and 6B are graphs showing a typical photoluminescence decay curve obtained with a photoluminescence lifetime spectrometer of the invention.
Figure 6B:
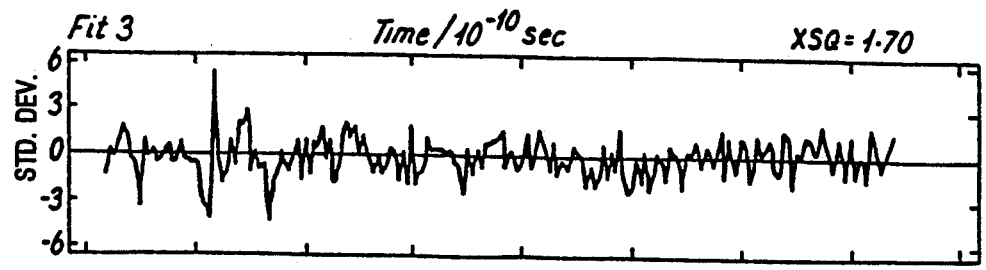

Finally FIGS. 6A and 6B show a typical photoluminescent decay characteristic curve for a Gallium Arsenide crystal obtained with a PLS of the invention such as shown in FIG. 1. As may be seen from this result, an instrumental response width of below 70 ps (FWHM) giving a time resolution of better than 10 ps and a spatial resolution of better than 3 $\mu$m allow the electrical characteristics of microscopic sample regions or very small devices to be investigated.

A typical application of great commercial interest is the in-line quality control of laser diodes. At present, the quality of laser diodes can only be tested at the final stage, i.e after growing (10–15 different steps), slicing, cleaving, packaging, bonding, encapsulating the device. It is known that the percentage of "scrap" devices is normally very high, up to 90% of the total output. Although fatal defects are most likely to be introduced during the initial growth steps, these defective devices are, at present, only revealed after actually operating the fully processed devices. Hence, the efficiency of the manufacturing process could be greatly enhanced by identifying faulty devices (or precursors thereof) at an early stage of manufacture through analysis of the photoluminescence time response charactertistics of the corresponding area of the GaAs crystal. The overall time required by a PLS-type system to test one device would be of the order of as little as several seconds.

The present invention also allows use of time-gated operation of a SPAD detector in electro-optic sampling as an alternative to using "slow" integrating photodiodes and boxcar signal averaging techniques for improving signal-to-noise performance. The same basic TCSPC set-up could be used as in the PLS instrument, except that the signal to be measured in electro-optic sampling is the change in intensity of the two plane polarization components after passing through the electrooptically active sample or probe device at the excitation wavelength of the pulsed excitation source.

The possibility of improved signal-to-noise (s/n) better overall system sensitivity and therefore shorter signal averaging time is due to the fact that a TCSPC detection system can be synchronised to the mode-locking frequency of the exciting laser source. A single analyser (SCA) is used for monitoring the TAC output signals with amplitudes corresponding to events within a narrow time range around the peak. The number of single photon events occurring within this narrow window are equivalent to the signal intensity measured with a slow, integrating photodiode (PD). The counting of single photons over many excitation pulses at 76–100 MHz corresponds to improving the pD s/n ratio by averaging over many lock-in cycles (several MHz).

The ratio of window width to repetition pulse spacing is a measure of the improvement in s/n of a fast single photon detector connected to a TAC and ADC/-SCA relative to a slow integrating detector. The width of the SCA window will depend on the instrumental response width of the TCSPC system, typically 60 ps (FWHM) with a SPAD detector. A 100 ps SCA window, e.g. improved s/n of a 100 MHz electro-optic sampling system with TCSPC detection relative to conventional detection by a factor of 100. before averaging.

Even signal averaging is faster in a TCSPC detection system because it occurs at the high mode-locking frequency, while the fastest choppers/lock-in amplifiers typically are limited to several MHz lock-in frequency and signal averaging is therefore much slower.

The external quantum efficiency of the current silicon SPAD at 1064 nm is very low, of the order of below 1%, such that little or no advantage is gained w.r.t. lock-in averaging systems based on slow integrating InGaAs or Ge PDs. However, application of Si-SPADs to the near infrared beyond 1064 nm will be possible with devices having separate absorption and avalanche multiplication regions, the latter consisting of e.g. an epitaxially grown strained layer $Si_{1-x}Ge_x$ superlattice structure on top of the Si-SPAD.

The improved sensitivity of a TCSPC detection system in electro-optic sampling may allow pulsed diode lasers to be used as excitation sources, as in photoluminescence lifetime spectroscopy.

The system described here, based on TCSPC, may be used together. The optical routing module may moreover conveniently be suitably extended, using another set of polarising beamsplitter cubes, to allow operation of a single instrument as a PLS or an EOS system.

Time-correlated single photon counting (TCSPC) systems for fluorescence/luminescence lifetime measurements use standard NIM timing electronics as in nuclear spectrocopy. The key component in any standard set-up is the time-to-amplitude converter (TAC)

TACs are designed for measuring the correlation between START and STOP signals derived from statistical events with very high precision. The integral and differential non-linearity are typically better than 0.1% and 0.5% respectively at input data rates up to 30 MHz for random signals. Use of TACs with continuous repetition rate sources, which is the case in fluorescence/luminescence lifetime experiments, however, results in decreased performance at much lower signal rates. The integral nonlinearity starts to increase significantly at below 10 MHz repetition rate and may easily reach more than ±5% at 100 MHz.

The stop-rate-reducer (SRR) circuit used in the preferred embodiment of the present invention (FIG. 2a) uses four cascaded constant fraction discriminators (CFD1-4) with fast VETO gates and four coaxial delay lines (DEL1-4), in a special arrangement in order to achieve the desired result. QUAD CFD units with fast VETO, e.g. the PhiliPs Mod. 714 CFD and variable coaxial delay lines are commercially available.

Three successive START pulses are shown in FIG. 2a. In this example, the second START pulse corresponds to the single STOP pulse, which is delayed w.r.t. START by δt. The START pulse is delayed w.r.t STOP by DEL1. This allows the GATE pulse triggered by the STOP pulse in CFD1 to overlap the leading edge of the shaped output from CFD2 present at the input of CFD3 width of the GATE pulse is precisely adjusted to be Δt, the START pulse spacing. Synchronisation of shaped START output from CFD2 and the GATE pulse from CFD1 is achieved by varying the delay DEL2. The START pulses corresponding to STOP pulses are now missing in the output form the gated CFD3. The CFD3 output is used to gate CFD4 which then produces the desired REDUCED START pulse train from shaped, delayed and synchronised second output of CFD1.

Thus in a further aspect the present invention provides gating device suitable for use in reducing a first very high speed periodic pulse train to a reduced pulse train containing only first pulses corresponding to the pulses of a second pulse train induced by respective ones of said first pulses with a variable time delay which device comprises a first pulse divider having primary and secondary and secondary outputs for primary and secondary first pulse trains, a second pulse extender for extending said second pulses to provide an extended second pulse train, a first fast gate means having an input for receiving said primary first pulse train and a gating input for receiving said extended second pulse train and disabling corresponding first pulses therein to provide a restricted output of first pulses without said corresponding first pulses, and a second fast gate means having an input for receiving the secondary first pulse train and a gating connection for receiving said restricted output of first pulses and disabling first pulses therein corresponding to said restricted output of first pulses so as to provide a reduced first pulse train containing only first pulses corresponding to said pulses of said second pulse train.

Thus by using extended second pulses it is possible to disable corresponding first pulses in the primary first pulse train despite the variable time delay and non-synchronised relation between the first and second pulse trains. The resulting restricted first pulse train being already synchronised with the secondary first pulse train, the former is readily employed selectively to disable all the first pulses thereof corresponding to the restricted first pulse train thereby providing a reduced first pulse train with only first pulses corresponding to the pulses of the second pulse train. With the arrangement of the present invention this can moreover be achieved at the very high repetition rates used in laser systems with frequencies as high as 50 MHz to 100 MHz.

Preferably the device includes second pulse divider means for providing a substantially non-extended second pulse train for comparison with said reduced first pulse train. Advantageously at least one of said fast gating means comprises a constant fraction discriminator, and preferably at least one of said pulse dividers and pulse extender comprises a constant fraction discriminator, with, most conveniently a single constant fraction discriminator providing the second pulse divider and pulse extender.

It will of course be appreciated that various mofifications may be made to the abovedescribed embodiments without departing from the scope of the present invention. Thus for example there may be used 'inverted' microscope arrangements wherein the sample is inspected from below rather than from above as illustrated, and indeed other arrangments with simultaneous inspection from both above and below may also be used.

I claim:

1. An optical routeing module device suitable for use in a light microscope for sample inspection simultaneously with a primary light source and a secondary light source of different wavlength to said primary light source, which device comprises a housing mounting first and second polarising beam splitter means along a primary light beam pathway through said device and having secondary light beam inlet and outlet means disposed opposite different, ones of said first and second polarising beam splitter means, said first and second polarising beam splitter means each having a narrow predetermined operating wavelength range, defined between s-plane and p-plane transitional wavelengths, which substantially excludes the primary light source wavelength band and is substantially above or below the wavelength band of said primary light source and such that the wavelength band of each of the secondary light source and a secondary light output from the sample responsive to incidence of said secondary light source on a said sample in use of the device is substantially below the s-plane transitional wavelength or above the p-plane transitional wavelength, of a respective one of said first and second polarising beam splitter means, respectively whereby, in use of the device, at least one polarising plane component of each of the secondary light source and said secondary light output is subjected to a different one of transmission and reflection from that to which the primary light source is subjected at each of the first and second polarising beam splitter means, said first and second polarising beam splitter means further being formed and arranged for defining a secondary light beam pathway from said inlet to said outlet so that the secondary light beam pathway is brought substantially into alignment with an outward leg of said primary beam pathway upstream of the sample by said first polarising beam splitter means and is separated back out from a return leg of said primary light beam pathway downstream of the sample by said second polarising beam splitter means whereby in use of the device in a light microscope, the area of incidence of the secondary light beam with the sample may be monitored via the primary light beam.

2. A device according to claim 1 wherein at least one of said first and second polarising beam splitter means has an operating wavelength range of longer wavelength than said primary light beam source and defines a primary light beam pathway section through itself by transmission.

3. A device according to claim 2 wherein said at least one of said first and second polarising beam splitter means defines a secondary light beam pathway for s-plane polarised light by reflection thereat.

4. A device according to claim 1 wherein at least one of said first and second polarising beam splitter means has an operating wavelength range of shorter wavelength than said primary light beam source and defines a primary light beam pathway section at itself, by reflection.

5. A device according to claim 4 wherein said at least one of said first and second polarising beam splitter means defines a secondary light beam pathway for p-plane polarised light by transmission thereat.

6. A device according to claim 1 wherein the wavelength band of at least one of the secondary light source and a secondary light output from the samples responsive to incidence of said secondary light source on a said sample in use of the device, is substantially within said predetermined operating wavelength range of a respective one of said first and second polarising beam splitter means.

7. A device according to claim 1 which includes at least one half-wave plate means formed and arranged for changing the plan of polarisation of a plane polarised secondary light beam approaching an associated polarising beam splitter means into a corresponding plane for a desired one of transmission through or reflection at said associated polarising beam splitter means.

8. A device according to claim 1 which includes at least one plane reflecting means formed and arranged for guiding at least one of the primary and secondary light beam pathways and reversing an image defined thereby.

9. A device according to claim 1 wherein the outward leg of said primary light beam pathway passes through said first polarising beam splitter means before said second polarising beam splitter means.

10. A device according to claim 1 wherein the operating wavelength ranges of said first and second polarising beam splitter means are at least partly offset relative to each other.

11. A device according to claim 1 wherein said polarising beam splitter means are formed and arranged so that said second polarising beam splitter means is crossed with respect to the first polarising beam splitter means or a combination of said first polarising beam splitter means with any polarising plane rotation means provided between said first and second polarising splitter means.

12. A device according to claim 1 wherein the operating wavelength range of each of said first and second polarising beam splitter means is longer than the primary light beam source wavelength and said first and second polarising beam splitter means are disposed along a substantially rectilinear primary light beam pathway with their principal planes crossed relative to each other whereby, in use, and s-plane polarised secondary light beam from said inlet is reflected at the first polarising beam splitter means substantially into alignment with the primary light beam pathway and s-plane polarised secondary light output beam approaching said second polarising beam splitter means is reflected thereat out of the primary light beam pathway towards said outlet.

13. An optical spectrometer device suitable for use in photoluminescence inspection of microscopic areas of microstructures which device comprises a light microscope having infinity corrected optics with a primary light beam pathway from a primary light source to a primary beam image output means, via a sample stage which primary light beam pathway has a substantially common portion extending towards and away from said sample stage, characterised in that there is provided an optical routeing module device according to claim 1 along said primary light beam pathway common portion, together with a secondary light beam source and a secondary light beam detector means coupled to respective ones of said secondary light beam inlet and outlet means of said module, whereby the position of incidence of said secondary light beam on said sample may be precisely directed by monitoring of said primary beam image output means.

14. A device according to claim 13 wherein said secondary light beam source is a laser source.

15. A device according to claim 14 wherein said laser source is a pulsed solid state laser source.

16. A device according to claim 15 wherein said laser source is coupled to said optical routeing module device secondary light beam inlet means via optical fibre means and said secondary light beam outlet means is coupled to said secondary light beam detector means by optical fibre means.

17. A device according to claim 13 wherein there is, coupled to the secondary light beam outlet means, at least one of a solid state detector, a fibre optic monochromator, and a wavelength-division-demultiplexer.

18. A device according to claim 13 wherein the secondary light beam detector means comprises a single photon avalanche diode detector.

19. A photoluminescent lifetime microscope spectrometer comprising a device according to claim 18 wherein said secondary light beam source is a pulsed solid state laser source and said single photon avalanche diode detector is connected to an anti-coincidence gating means coupled to the pulsed solid laser source and formed and arranged for providing, in use, an output corresponding to laser source excitation pulses in which output all laser source excitation pulses for which no secondary light output pulse from the sample is obtained, have been eliminated.

20. A spectrometer according to claim 19 wherein said optical routeing module is formed and arranged so that said secondary light source beam is incident with said sample at an angle in the region of the Brewster angle thereof.

21. A spectrometer according to claim 19 wherein said gating means comprises first and second discriminator pulse processing means for receiving respective ones of an excitation signal input comprising a series of pulses corresponding to the laser source secondary light beam pulses and a detector signal output comprising a series of pulses corresponding to secondary light output pulses induced by incidence of said laser source pulses with the sample in use of the device, said first pulse processing means being formed and arranged for providing first and second outputs comprising a first series of pulses corresponding to the laser source pulses substantially free of interference, said second pulse processing means being formed and arranged for providing a first output comprising a second series of pulses corresponding to secondary light output pulses substantially free of interference and a second output comprising a second series of gate pulses for respective ones of said secondary light output pulses temporally extended to not longer than the period between successive said laser pulses; a third pulse processing means formed and arranged for receiving the second output of said first pulse processing means and said gate pulses and providing a modified output corresponding to said first series of pulses from which have been removed, by said gate pulses, those pulses associated with said secondary light output pulses thereby providing an anti-coincidence series of pulses; and a fourth pulse processing means formed and arranged for receiving said first output comprising a said first series of pulses and said modified output comprising said anti-coincidence series of pulses, and combining them so as to provide a reduced output comprising pulses corresponding to only those of said laser pulses for which a secondary light output pulse has been received, said gating means further including pulse delay means formed and arranged for providing said first output of secondary light output pulses in the same temporal relationship to said reduced output of pulses corresponding to corresponding laser pulses, as in the excitation signal input and detector signal output whereby monitoring of said temporal relation is substantially free of interference from excitation signals for which no detector signal output is received.

22. A device according to claim 1 wherein at least one of said first and second polarising beam splitter means is slightly bevelled and/or tilted relative to the primary light beam pathway thereby to reduce unwanted reflections when used with a small system aperture.

23. A device according to claim 22 wherein is used a system stop aperture generally in the image plane of from 5 to 50 um in diameter.

24. A spectrometer according to claim 22 wherein said single photon detector and gating means are connected to a time-amplitude converter means formed and arranged for converting the time delay between individual laser source excitation pulses and their corresponding secondary light output pulses, into analogue signals.

25. A method of simultaneous microsopic sample inspection with primary and secondary light sources of different wavelengths, which method comprises the steps of providing first and second polarising beam splitter means along a primary light beam pathway of an optical microscope, said first and second polarising beam splitter means each having a narrow predetermined operating wavelength range which substantially includes a respective one of the secondary light source and a secondary light output from the sample responsive to incidence of said secondary light source on a said sample in use of the device, and excludes said primary light source; bringing a secondary light beam pathway from said secondary light source substantially into alignment with the primary light beam pathway at said first polarising beam splitter means and separating at least part of said secondary light beam pathway out of said primary light beam pathway at said second polarising beam splitter means, and detecting the separated out secondary light beam output.

* * * * *